United States Patent [19]

Noetzel et al.

[11] 4,111,900

[45] Sep. 5, 1978

[54] BROMINE-CONTAINING PHOSPHINIC ACID ESTERS AND FLAME-RESISTANT PLASTIC MOLDING COMPOSITIONS

[75] Inventors: Siegfried Noetzel, Kelkheim, Taunus; Horst Jastrow, Niederhöchstadt, Taunus; Rudolf Uebe, Hofheim, Taunus, all of Fed. Rep. of Germany

[73] Assignee: Hoechst Aktiengesellschaft, Frankfurt am Main, Fed. Rep. of Germany

[21] Appl. No.: 724,252

[22] Filed: Sep. 17, 1976

[30] Foreign Application Priority Data

Sep. 20, 1975 [DE]  Fed. Rep. of Germany ....... 2542009

[51] Int. Cl.$^2$ ................................................ C07F 9/32
[52] U.S. Cl. ................................ 260/45.7 P; 260/928; 260/930; 260/952; 260/956; 260/957; 260/958; 260/961
[58] Field of Search ........... 260/956, 958, 961, 45.7 P, 260/961

[56] References Cited

U.S. PATENT DOCUMENTS

| 3,324,205 | 6/1967 | Carpenter et al. | 260/961 X |
|---|---|---|---|
| 3,991,010 | 11/1976 | Noetzel et al. | 260/45.7 P |

FOREIGN PATENT DOCUMENTS 362,023  12/1973  U.S.S.R. .................................. 260/961

OTHER PUBLICATIONS

Derwent's Central Patent Index, Sec. A, Plasdoc, vol. W, Nos. 19, 25 and 30 (1975).
Ogawa et al., Chemical Abstracts, vol. 81 (1974) 4070t.

*Primary Examiner*—Richard L. Raymond
*Attorney, Agent, or Firm*—Curtis, Morris & Safford

[57] ABSTRACT

There are disclosed novel flame-proofing agents for plastics, especially for homopolymers and copolymers of styrene and acrylonitrile. These agents are organic compounds containing bromine and one or two phosphinic acid groups. Besides the good flame-retarding properties these compounds have the advantage that they do not adversely affect the shrinking of foamed plastics.

6 Claims, No Drawings

BROMINE-CONTAINING PHOSPHINIC ACID ESTERS AND FLAME-RESISTANT PLASTIC MOLDING COMPOSITIONS

This invention relates to bromine-containing phosphinic acid esters suitable as flame proofing agents for plastics materials.

It is known that readily inflammable plastics can be rendered flame resistant by the addition of halogen compounds. Flame resistant plastics compositions are especially interesting for the manufacture of porous thermoplastics, for example cellular plastics on the basis of styrene polymers.

Halogen compounds suitable for rendering plastics flame resistant are, for example, highly chlorinated non volatile hydrocarbons which are used preferably in combination with antimony trioxide. A disadvantage of these chlorinated hydrocarbons is the fact that they must be used in a relatively large amount, in general 15 to 20% by weight, calculated on the plastic material, to obtain a satisfactory flame resistance. In the manufacture of foamed articles from foamable granular thermoplastics this drawback is especially disturbing. The high proportion of halogen compounds hinders the welding of the granular material and in many cases cellular plastics of low mechanical strength are obtained.

It is also known that organic bromine compounds are much more effective than the corresponding chlorine compounds. It is not possible, however, to use every bromine compound as flame proofing agent. Bromine compounds which are suitable to render plastics resistant to burning are, for example, tetrabromobutane, dibromoethyl benzene, dibromopropanol, tris(2,3-dibromopropyl) phosphate, 2-bromoethyl-phosphonic acid bis(2-bromoethyl) ester, tetrabromocyclooctane, or hexabromocyclododecane. They are generally used in an amount of from 5 to 10% by weight, calculated on the plastics material.

A compound well suited for rendering plastics flame proof should mainly have the following properties: it should have a low volatility and be free from odor, should not detrimentally affect the mechanical properties of the plastics material and should exhibit a good effect when used in as small a quantity as possible. Furthermore, it should not promote corrosion and it should be capable of being added to the monomers prior to polymerization without the course of polymerization being hindered. A prerequisite for this is that the bromine compound is readily soluble in the monomer to be polymerized, for example in styrene.

Organic bromine compounds known for their flame-proofing effect rarely have all these properties to a sufficient extent. Some of them are volatile so that the flame resistance of the plastics treated therewith is lost after a time and some of them have an unpleasant odor. Many of the known bromine compounds have a plasticizing effect. For the manufacture of cellular plastics from foamable granular thermoplastic compositions flameproofing agents having a plasticizing effect are unsuitable since they yield foamed articles having a poor pressure resistance and volume constancy. Finally, most of the organic bromine compounds retard the polymerization of polymerizable monomers and therefore, they can only be mixed with the polymer and not with the monomers. And in many cases their solubility in the polymerizable monomer is so poor, for example in styrene, that an addition during polymerization cannot be taken into consideration. Many flame-proofing agents are soluble in the polymerizing monomers but owing to their incompatibility with the polymer they crystallize so that the flame resistance is reduced.

The present invention provides bromine-containing phosphinic acid esters of the general formulae

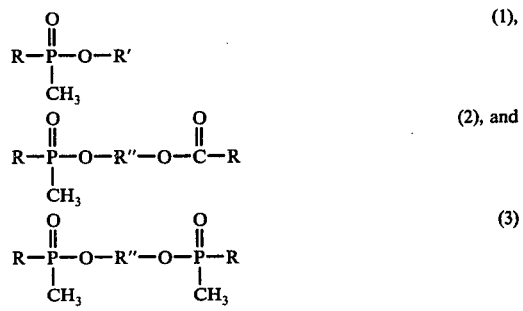

in which

R represents identical or different, bromine-containing linear or branched aliphatic hydrocarbon radicals optionally having a double bond and containing 2 to 12, preferably 2 to 6, carbon atoms and/or bromine-containing cycloaliphatic hydrocarbon radicals having 4 to 10, preferably 5 to 8, carbon atoms, optionally carrying alkyl substituent(s) and/or containing a double bond;

R' represents an alkyl group which is unsubstituted or substituted by bromine atoms and optionally branched and contains 2 to 12, preferably 2 to 6, carbon atoms, or a cycloaliphatic or aromatic radical having 6 to 12 carbon atoms which is unsubstituted or substituted by halogen atoms, preferably bromine atoms, and optionally also by alkyl radicals; and R" represents an alkylene radical which is unsubstituted or substituted by bromine atoms and optionally branched and contains 2 to 12, preferably 2 to 6, carbon atoms, or a bivalent cycloaliphatic or aromatic radical having from 6 to 12 carbon atoms which is unsubstituted or substituted by bromine atoms and optionally by alkyl groups.

This invention also provides flame resistant plastics molding compositions containing as flame-proofing agent 0.3 to 10, preferably 0.5 to 6% by weight, calculated on the plastics composition, of a bromine-containing organic phosphinic acid ester of the formulae

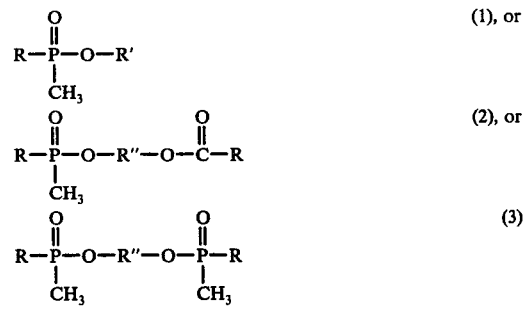

in which R, R' and R" have the above meaning.

Besides the bromine atoms in the radical(s) R the flame-proofing agents of the invention may also contain chlorine atoms as substituents in the radical(s) R and/or R' or R".

The crystalline 2,4,6-tribromo- and 2,4,6-trichlorophenolic esters of 1,2-dibromoethyl-phosphinic acid were found to be especially effective.

The phosphinic acid esters according to the invention are prepared by known methods. According to one method 1 mol of an unsaturated methylphosphinic acid chloride, for example vinylmethyl-phosphinic acid chloride, is reacted in a solvent, for example chloroform, at 0° to 5° C. with 1 mol of a primary, secondary or tertiary alcohol or of a phenol in the presence of 1 mol of triethyl amine. The unsaturated methylphosphinic acid esters obtained in a good yield, for example vinylmethyl phosphinic acid esters, absorb in chloroform at room temperature within about 5 hours the required equivalents of bromine with formation of the saturated bromine-containing methylphosphinic acid esters, for example dibromoethylmethyl phosphinic acid ester.

It is also possible to add 1 mol of a diene, for example butadiene-1,3 or cyclopentadiene, on the vinyl group of the vinylmethyl phosphinic acid chloride by heating to 150° to 200° C., optionally under pressure; the Diels-Alder addition product obtained is then esterified as described above and subsequently brominated.

The flame-proofing phosphinic acid esters of the invention are free from odor. At room temperature they practically have no vapor pressure and thus do not evaporate. Flame resistant compositions containing the aforesaid compounds do not lose their flame resistance even after a prolonged storage period.

As compared with the brominated phosphoric acid esters described in German patent specification No. 1,046,313, the phosphinic acid esters of the invention are much more stable to hydrolysis.

The phosphinic acid esters of the invention are well compatible with a series of plastics, for example polystyrene or polyacrylonitrile. They can be used to render flame-resistant all readily inflammable plastics such as polymers and copolymers or ethylene, propylene, acrylic acid esters, methacrylic acid esters and vinyl acetate, or curable resins such as unsaturated polyester resins, or polyaddition products, for example polyurethanes. The compounds of the invention are especially suitable for rendering flame resistant styrene polymers such as polystyrene and copolymers of styrene and acrylonitrile or/and butadiene-1,3, as well as acrylonitrile polymers such as polyacrylonitrile and copolymers of acrylonitrile and vinyl chloride or vinylidene chloride.

A further advantage of the phosphinic acid esters of the invention resides in the fact that they do not affect the shrinking properties of foamed blocks of plastics material, for example of polystyrene. Moreover, the phosphinic acid esters of the invention can be added to the plastics material in a smaller quantity than the brominated phosphonic acid esters of formula X—R—P—(O—R—X)$_2$, known for example from German Offenlegungsschrift No. 1,495,419, and the brominated butadiene polymers, described for example in German patent specification No. 1,218,149, for obtaining the same degree of flame resistance.

The flame resistant compositions of the invention can be prepared by different methods. An intimate mixture of the plastics material with the flame-proofing agent according to the invention can be obtained by mixing the two components in the heat, but at a temperature below 170° C., in an extruder or kneader. Alternatively, the two components can be dissolved in a mutual solvent which is subsequently removed. An advantageous mode of preparation consists in polymerizing the monomers in the presence of the flame-proofing compound and optionally in the presence of peroxides which decompose at higher temperatures and are known as synergistic auxiliaries, for example di-tert-butyl peroxide. This mode of operation is especially interesting for the manufacture of small sized, difficultly inflammable and expandable styrene polymers by polymerizing styrene, preferably in aqueous suspension, in the presence of readily volatile aliphatic hydrocarbons or their fluorinated and/or chlorinated derivatives as expanding agent.

In other processes, instead of preparing an intimate mixture, the granular or bead-shaped polymer is coated with the flame-proofing agent. This method is especially important with expandable granular masses, especially small sized expandable styrene polymers, containing readily volatile aliphatic hydrocarbons or the halogen derivatives thereof as expanding agent. Some of the methods suitable for preparing flame resistant compositions are described in detail in the following examples.

The addition of peroxides is also advantageous when the bromine compounds are added to the finished polymer. There are preferably used peroxides having a half life period of at least 2 hours at 100° C. (measured in benzene), for example dicumyl peroxide, tert-butyl hydroperoxide, ditert-butyl peroxide, pinane hydroperoxide, and cumyl hydroperoxide. Mixtures of two or more of the peroxides may also be used as synergist.

The following examples illustrate the invention.

EXAMPLE 1 a. Preparation of vinylmethyl phosphinic acid allyl ester 202 g of triethyl amine (2 mols) were added while stirring at 0° to 5° C. to a solution of 116 g of allyl alcohol (2 mols) in 1 l of anhydrous chloroform and then 249 g of methylvinyl phosphinic acid chloride (2 mols) were added dropwise over a period of about 1 hour. After suction filtration, the solid residue (triethyl amine hydrochloride) was dissolved in water, the emerging oily layer was separated and combined with the filtrate. To remove the chloride ions the filtrate was shaken 4 times, each time with 600 ml of water, dried over sodium sulfate and the chloroform was distilled off in a rotary evaporator. The brown oily residue was distilled under a pressure of 0.01 mm at a temperature of the oil bath of 40° C. 85 g of a colorless liquid were obtained.

b. Bromination of vinylmethyl phosphinic acid allyl ester 73 g of vinylmethyl phosphinic acid allyl ester (0.5 mol) were dissolved in 300 ml of chloroform and a solution of 160 g of bromine (1 mol) in 200 ml of chloroform was added dropwise at 0° to 10° C. over a period of 30 minutes. Half of the bromine solution was discolored immediately on being dropped in. The reaction mixture was kept overnight at 25° C. and then boiled with the addition of active carbon. After removal of the active carbon by filtration and distillation of the chloroform a slightly grey viscous oil was obtained.

Molecular weight: 466, corresponding to the theoretical formula $C_6H_{11}O_2PBr_4$ Analysis:
calculated: 15.5% C; 2.3% H; 6.6% P; 68.7% Br;
found: 15.3% C; 2.1% H; 6.3% P; 68.8% Br.

EXAMPLES 2 to 12

The compounds listed in Table 1 were prepared by reacting vinylmethyl phosphinic acid chloride with the alcohol or phenol specified in column 2 of said table with subsequent bromination under the conditions described in Examples 1 (a) and (b). For the preparation of the compound of Example 3 bromine was added on vinylmethyl phosphinic acid chloride and the resulting addition product was reacted with 2-hydroxyethyl-methacrylate. The compound of Example 1 is also listed in Table 1.

Table 1

| Ex. | alcohol, phenol structure | 1,2-dibromoethylmethyl phosphinic acid ester structure | constitution |
|---|---|---|---|
| 1 | $CH_2=CH-CH_2OH$ | $CH_2-CHBr-P(=O)(CH_3)-O-CH_2CHBr-CH_2Br$ (with Br on first CH$_2$) | viscous oil |
| 2 | hydroxy-dicyclopentadiene (HO-tricyclic structure) | corresponding phosphinic ester with dibrominated tricyclic group | viscous oil |
| 3 | $CH_2=C(CH_3)-C(=O)-O-CH_2CH_2OH$ | $CH_2Br-CHBr-P(=O)(CH_3)-O-CH_2-CH_2-O-C(=O)-C(CH_3)=CH_2$ | oily liquid |
| 4 | phenol (C$_6$H$_5$OH) | $CH_2Br-CHBr-P(=O)(CH_3)-O-C_6H_5$ | viscous oil |
| 5 | 4-tert-butylphenol ((CH$_3$)$_3$C-C$_6$H$_4$-OH) | $CH_2Br-CHBr-P(=O)(CH_3)-O-C_6H_4-C(CH_3)_3$ | viscous oil |
| 6 | 2-naphthol | $CH_2Br-CHBr-P(=O)(CH_3)-O$-(2-naphthyl) | viscous oil |
| 7 | 2,4,6-trichlorophenol | $CH_2Br-CHBr-P(=O)(CH_3)-O$-(2,4,6-trichlorophenyl) | crystalline (melting point 167° C) |
| 8 | 2,4,6-tribromophenol | $CH_2Br-CHBr-P(=O)(CH_3)-O$-(2,4,6-tribromophenyl) | crystalline (melting point 157° C) |
| 9 | pentabromophenol | $CH_2Br-CHBr-P(=O)(CH_3)-O$-(pentabromophenyl) | crystalline (melting point (crude) 190° C) |
| 10 | hydroquinone (HO-C$_6$H$_4$-OH) | $CH_2Br-CHBr-P(=O)(CH_3)-O-C_6H_4-O-P(=O)(CH_3)-CHBr-CH_2Br$ | viscous mass |
| 11 | bisphenol A (HO-C$_6$H$_4$-C(CH$_3$)$_2$-C$_6$H$_4$-OH) | $CH_2Br-CHBr-P(=O)(CH_3)-O-C_6H_4-C(CH_3)_2-C_6H_4-O-P(=O)(CH_3)-CHBr-CH_2Br$ | viscous mass |

Table 1-continued

| Ex. | alcohol, phenol structure | 1,2-dibromoethylmethyl phosphinic acid ester structure | constitution |
|---|---|---|---|
| 12 | HO—[Br,Br-C6H2]—C(CH3)2—[Br,Br-C6H2]—OH | CH2CH(Br)(Br)—P(=O)(CH3)—O—[Br,Br-C6H2]—C(CH3)2—[Br,Br-C6H2]—O—P(=O)(CH3)—CH(Br)—CH2Br | viscous mass |

Preparation of flame-resistant plastics with dibromoethylmethyl phosphinic acid esters

EXAMPLE 13 a. Comparative example according to the state of the art

A 20% by weight solution of polystyrene (reduced specific viscosity 1.4 dl/g, measured with a solution of 1 g of polystyrene in 100 ml benzene at 25° C.) in methylene chloride was prepared. 100 g of this solution were mixed while stirring with 0.68 g of 1,2,5,6,9,10-hexabromocyclododecane, corresponding to 0.5% by weight of bromine, and 0.1% by weight of tertbutyl hydroperoxide, the mixture was poured into a dish made of an aluminum foil (19 × 8 × 2 cm) and stored for 12 hours under the hood. After flattening of the aluminum foil the polystyrene sheet was covered by another aluminum foil and the whole was placed in a perforated steel mold which was plunged into boiling water for 20 minutes. The foamed sheet was dried for 12 hours at 70° C. in a vacuum drier while introducing a weak nitrogen current.

Burning test: The foamed sheet was fixed in a position such that its smaller side formed an angle of 45° with respect to the horizontal. The longitudinal edge in lower position was exposed successively at three different points, each time for 5 seconds, to the action of a non-luminous flame about 5 cm height of a Bunsen burner. Next, the sheet was turned by 90° to bring the upper longitudinal edge into the lower position and this edge was exposed to the flame in the same manner. When the flame was cautiously removed in each case the sheet continued to burn for more than 20 seconds.

b. Example according to the invention

A 20% by weight solution of polystyrene (reduced specific viscosity 1.4 dl/g in a solution of 1 g of polystyrene in 100 ml of benzene at 25° C.) in methylene chloride was prepared. 100 g of this solution were mixed while stirring with 0.15 g of 1,2-dibromoethylmethyl phosphinic acid 2,3-dibromopropyl ester, corresponding to 0.5% by weight of bromine, and 0.1% by weight of tert-butyl hydroperoxide, the mixture was poured into a dish made of an aluminum foil (19 × 8 × 2 cm) and kept for 12 hours under the hood. The sheet obtained was then foamed, dried and exposed to the flame as described in Example 13 a and the extinguishing time after the removal of the flame was measured. The sheet stopped burning after 5 to 9 seconds.

EXAMPLES 14 to 24

Under the conditions specified in Example 13(b) cast sheets were prepared with the compounds listed in Table 1 and the burning test was carried out under the conditions of Example 13(a). The concentration of the bromine compound in the polystyrene sheet was calculated to 0.5% of bromine. In Examples 20, 21 and 24 the bromine content of 0.5% by weight refers to the aliphatically bound bromine. In each case 0.1% by weight of tertbutyl hydroperoxide were added. The extinguishing time after the removal of the flame from the foamed sheet was measured with a stop-watch. The results are listed in the following Table 2.

TABLE 2

| Example | Flame proofing compound structure | content in polystyrene sheet (%) (+ 0.1 % t-butyl hydroperoxide) | burning test extinguishing time (seconds) |
|---|---|---|---|
| 13a | hexabromocyclododecane (comparison) | 0.67 | >20 |
| 13b | CH2(Br)—CH(Br)—P(=O)(CH3)—O—CH2—CH(Br)—CH2(Br) | 0.72 | 5–9 |
| 14 | CH2(Br)—CH(Br)—P(=O)(CH3)—O—[dibromonorbornyl] | 0.86 | 2–4 |
| 15 | CH2(Br)—CH(Br)—P(=O)(CH3)—O—CH2—CH2—O—C(=O)—C(CH3)=CH2 | 0.89 | 7–12 |

TABLE 2-continued

| Example | Flame proofing compound structure | content in polystyrene sheet (%) (+ 0.1 % t-butyl hydroperoxide) | burning test extinguishing time (seconds) |
|---|---|---|---|
| 16 | $CH_2-CH-P(=O)(CH_3)-O-C_6H_5$ with Br, Br substituents | 1.1 | 6–11 |
| 17 | $CH_2-CH-P(=O)(CH_3)-O-C_6H_4-C(CH_3)_3$ with Br, Br substituents | 1.3 | 5–10 |
| 18 | $CH_2-CH-P(=O)(CH_3)-O-$naphthyl with Br, Br substituents | 1.2 | 5–8 |
| 19 | $CH_2-CH-P(=O)(CH_3)-O-C_6H_2Cl_3$ with Br, Br substituents | 1.4 | <1–2 |
| 20 | $CH_2-CH-P(=O)(CH_3)-O-C_6H_2Br_3$ with Br, Br substituents | 1.8 | <1–2 |
| 21 | $CH_2-CH-P(=O)(CH_3)-O-C_6Br_5$ with Br, Br substituents | 2.4 | 2–4 |
| 22 | $CH_2-CH-P(=O)(CH_3)-O-C_6H_4-O-P(=O)(CH_3)-CH-CH_2$ with Br, Br and Br, Br substituents | 1.0 | 2–7 |
| 23 | $CH_2-CH-P(=O)(CH_3)-O-C_6H_4-C(CH_3)_2-C_6H_4-O-P(=O)(CH_3)-CH-CH_2$ with Br, Br and Br, Br substituents | 1.1 | 2–8 |
| 24 | $CH_2-CH-P(=O)(CH_3)-O-C_6H_4-C(CH_3)_2-C_6H_4-O-P(=O)(CH_3)-CH-CH_2$ with Br, Br and Br, Br substituents | 1.6 | 1–9 |

EXAMPLE 25 a. Comparative Example according to the state of the art 230 ml each of softened water and styrene were introduced into a 1 liter round glass flask, the contents of the flask were heated to 90° C. while stirring and a solution of 0.27% by weight of dibenzoyl peroxide, 0.81% by weight of 1,2,5,6,9,10-hexabromocyclododecane, corresponding to 0.6% by weight of bromine, and 0.2% by weight of di-tert-butyl peroxide in 45 ml of styrene was added.

After polymerization of 54% of the monomeric styrene, a solution of 0.75 g of a commercial polyvinyl alcohol (having a residual ester content of about 15%) in 50 ml of water was added yielding a stable dispersion. The suspension polymerization was carried out while stirring for 8 hours at 90° C. After separation of the aqueous phase, the polymer beads were washed with water, isolated and dried for 12 hours in air at room temperature. Next, a 20% by weight solution of the polymer in methylene chloride was prepared. In the manner described in Example 13(a) a foamed sheet was prepared from 100 g of the solution obtained and exposed to the flame at 6 points. The extinguishing times found were in the range of from 3 to 13 seconds.

b. According to the invention

A 1 liter round glass flask was charged with 230 ml each of softened water and styrene, the contents of the flask were heated to 90° C. and a solution of 0.27% by weight of dibenzoyl peroxide, 1.4% by weight of 1,2- dibromoethylmethyl phosphinic acid 2,4,6-trichlorophenyl ester, corresponding to 0.5% by weight of bromine, and 0.2% by weight of di-tert-butyl peroxide in 45 ml of styrene was added.

After polymerization of 54% of the monomeric styrene a solution of 0.75 g of a commercial polyvinyl alcohol (having a residual ester content of about 15%) in 15 ml of water were added yielding a stable dispersion. Suspension polymerization was carried out for 8 hours at 90° C. After separation of the aqueous phase the polymer beads were washed with water, isolated and dried for 12 hours in air at room temperature. Next, a 20% by weight solution of the polymer in methylene chloride was prepared. Under the conditions of Example 13(a) a foamed sheet was prepared from 100 g of the solution and subjected to the burning test. The extinguis-hing times were found to be <1, <1, <1, 1, 1, and 1 second.

EXAMPLE 26

A flame resistant composition was prepared under the conditions of Example 25(b) with the exception that the 1.4% by weight of 1,2-dibromoethylmethyl phosphinic acid 2,4,6-trichlorophenyl ester, corresponding to 0.5% by weight of bromine, were replaced by 1.4% by weight of 1,2-dibromoethylmethyl phosphinic acid 2,4,6-tribromophenyl ester, corresponding to 0.4% by weight of aliphatically bound bromine. The burning test of the foamed sheet gave the following extinguishing times: <1, <1, 1, 2, 2, and 2 seconds.

EXAMPLE 27

A flame resistant composition was prepared under the conditions of Example 25(b) with the exception that 1.4% by weight of 1,2-dibromoethylmethyl phosphinic acid 2,4,6-trichlorophenyl ester, corresponding to 0.5% by weight of bromine, were replaced by 1.1% by weight of the compound of Example 2, corresponding to 0.6% by weight of bromine. The burning test of the foamed sheet gave the following extinguishing times: 1, 1.5, 1, 1, 1, and 1 second.

EXAMPLE 28

6.0 parts by weight of 1,2-dibromoethylmethyl phosphinic acid 2,4,6-tribromophenyl ester and 0.5 part by weight of dibenzoyl peroxide were dissolved in a mixture of 70 parts by weight of styrene and 30 parts by weight of acrylonitrile. The solution was suspended in 200 parts by weight of water containing 0.8 g of barium sulfate as suspension stabilizer and polymerized for 20 hours at 70° C. and 10 hours at 80° C. The polymer particles were separated, washed and dried and molded at 160° C. into 1.6 mm thick plates from which test specimens of 127 × 12.7 × 1.3 mm were cut. The test specimens clamped in horizontal position were exposed at their free ends for 30 seconds to the non luminous flame of a Bunsen burner according to ASTM D 635-68. The test specimens burned beyond the first marking, which was about 25 mm remote from the free end, and extinguished after 50 mm of the specimens had burned. According to the ASTM D 635-68 prescription the product can be considered self extinguishing.

EXAMPLE 29

A flame resistant composition was prepared under the conditions of Example 25(b) with the exception that instead of 1.4% by weight of 1,2-dibromoethylmethyl phosphinic acid 2,4,6-trichlorophenyl ester 0.8% by weight of 1,2-dibromo-ethylmethyl phosphinic acid ester of hydroxyethyl methacrylate (of Example 3) was used as flame-proofing agent according to the invention. This compound having a double bond was copolymerized with the styrene. The burning test under the conditions of Example 13(a) with the foamed sheet showed extinguishing times of 8 to 14 seconds.

What is claimed is:

1. Bromine-containing phosphinic acid esters of the formula

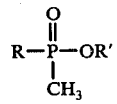

wherein
R represents 1,2-dibromoethyl and
R' represents 2,4,6-tribromophenyl or 2,4,6-trichlorophenyl.

2. A flame-resistant plastic molding composition containing as a flame-proofing agent from 0.3 to 10% by weight, based on the weight of the plastic composition, of a bromine-containing organic phosphinic acid ester of the formula

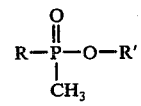

in which R is selected from linear and branched, bromine-containing aliphatic hydrocarbon radicals of 2 to 12 carbon atoms which may contain a double bond, and bromine-containing cycloaliphatic hydrocarbon radicals of 4 to 10 carbon atoms which may be alkyl-substituted and may contain a double bond, and R' is selected from bromine-substituted, linear and branched alkyl groups of 2 to 12 carbon atoms and halogen-substituted cycloaliphatic and aromatic hydrocarbon radicals of 6 to 12 carbon atoms which may be alkyl-substituted.

3. A flame-resistant plastic molding composition according to claim 2 containing from 0.5 to 6% by weight of said bromine-containing organic phosphinic acid ester.

4. Flame resistant plastics molding composition as claimed in claim 2, which contains, in addition to the flame-proofing agent, an organic peroxide as synergist.

5. Flame resistant plastics molding composition as claimed in claim 2, wherein the plastic is polystyrene, a copolymer of styrene and acrylonitrile, a copolymer of styrene, butadiene-1,3 and acrylonitrile, polyacrylonitrile, a copolymer of acrylonitrile and vinyl chloride, or a copolymer of acrylonitrile and vinylidene chloride.

6. Flame resistant plastics molding composition containing as flame-proofing agent a phosphinic acid ester of the formula

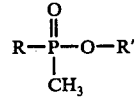

wherein
R represents 1,2-dibromoethyl and
R' represents 2,4,6-tribromophenyl or 2,4,6-trichlorophenyl.

* * * * *